United States Patent [19]
Baron

[11] Patent Number: 5,387,202
[45] Date of Patent: Feb. 7, 1995

[54] EYE DROP DISPENSING DEVICE

[75] Inventor: Brian F. Baron, Largo, Fla.

[73] Assignee: Aaron Medical Industries, St. Petersburg, Fla.

[21] Appl. No.: 254,487

[22] Filed: Jun. 6, 1994

Related U.S. Application Data

[63] Continuation of Ser. No. 88,094, Jul. 1, 1993, abandoned, which is a continuation of Ser. No. 915,299, Jul. 20, 1992, abandoned.

[51] Int. Cl.[6] .............................................. A61M 35/00
[52] U.S. Cl. ..................................... 604/300; 604/302
[58] Field of Search ............... 604/289, 294, 295, 300, 604/301, 302

[56] References Cited

U.S. PATENT DOCUMENTS 2,705,959  4/1955  Elmore ..................... 128/207.14
3,872,865  3/1975  Casey ............................ 604/302
4,664,109  5/1987  Rasocha .................... 128/207.14

Primary Examiner—Randy C. Shay
Attorney, Agent, or Firm—A. W. Fisher, III

[57] ABSTRACT

An eye drop dispensing device for use with a pliable ophthalmic solution container retaining an optic solution therein including a dispensing nozzle to dispense eye drops from the pliable opthalmic solution container comprising a pliable housing having an eyelid engaging rim formed on one end thereof and including a channel formed therethrough to receive and house the dispensing nozzle and a major portion of the pliable ophthalmic solution container therein such that the eyelid engaging rim is placed on the face and eyelid of a person with the dispensing nozzle adjacent the person's eye to permit depression of the pliable housing and pliable ophthalmic solution container to dispense solution directly into the user's eye while holding the eyelid open.

1 Claim, 2 Drawing Sheets

EYE DROP DISPENSING DEVICE

CO-PENDING APPLICATION

This application is a continuation application of Ser. No. 088,094 filed Jul. 1, 1993, now abandoned, which is a continuation of application Ser. No. 915,299 filed Jul. 20, 1992 now abandoned.

BACKGROUND OF THE INVENTION

1. Field of the Invention

An eye drop dispensing device for use with a pliable ophthalmic solution container to dispense or administer eye drops.

2. Description of the Prior Art

Most people encounter difficulty in applying drops to their eyes due to the extreme sensitivity of them. The eye is sensitive. Thus nomally individuals find it difficult to control reflexive blinking when applying eye drops. Moreover poor vision makes it difficult to properly position or align an eye dropper bottle relative to the eye frequently causes drops to be improperly applied.

Thus applying eye drops is generally difficult, uncomfortable and resulted in little, if any, of each drop entering the eye so that several attempts were necessary to insure placement of the ophthalmic solution in the eye. As a result, considerable amounts of the solution were wasted with no real assurance that a prescribed or desired amount of solution was placed in the eye.

U.S. Pat. No. 4,543,096 describes an apparatus having finger like projections attached to the front of an eye drop bottle to spread the eyelids apart apart during the eye drop dispensing process. One moveable finger is connected to a lever to depress the lever and simultaneously causing the eyelids to spread apart while forcing a drop from the dropper bottle.

U.S. Pat. No. 4,792,334 discloses an occular treatment apparatus for applying a liquid from a reservoir comprising a tubular housing with a first open end adapted to conform to the shape of the facial area surrounding the eye socket constructed to receive, hold and position the liquid. A sighting opening is included on the housing to properly orient the eye and distract the user from the drops of liquid to be introduced into the eye. An eyelid displacement mechanism is supported on the first open end of the housing at a position diametrically opposed to the sighting opening to expose the cul de sac. As a result, the liquid dispensed into the eye will more easily and directly be applied at or near the cul de sac.

U.S. Pat. No. 3,279,466 shows an eye drop dispensing aid comprising an elongated base having means for connection to an eye drop cotnainer, eyelid engaging means and support means connecting the eyelid engaging means to the base. The support means extend from the base parallel to the longitudinal axis of the base and supporting the eyelid engaging means spaced outwardly from the base, while the eyelid engaging means includes a first arcuate surface in a plane transverse to the longitudinal axis and having opposite free ends which are spaced apart in the plane including a surface arcuate in a direction generally normal to the plane and projecting from generally between the free ends of the first arcuate surface and outwardly therefrom.

U.S. Pat. No. 2,898,911 teaches an opthalmic dispenser comprising a medicament container having an outlet nozzle for ejecting drops of the medicament. An eye cup having a base and an outer lip shaped to conform to the portion of the user's face about the periphery of the eye ball is connected to the container with the nozzle extending a short distance into the eye cup to permit the nozzle to assume a position a short distance away from the eye ball when the cup is placed in contact with the portion of the user's face about the periphery of the eye ball.

U.S. Pat. No. 2,482,431 describes an eye cup with a rim portion around the lower edge thereof to fit comfortably against the eye socket. The bottom of the cup includes an aperture to frictionally retain a resilient sleeve and a flanged portion that permits convenient gripping of the body by the user. Removably carried within the sleeve is a tubular, open-ended, member provided with an annular rim that is secured to a sac including an integral shoulder that bears against sleeve for correct positioning of the member in the cup. A tubular glass insert open at its ends, is positioned within the member, has one end reduced to engage a reduced opening in the member and the other end of the insert is rounded to conform to the rounded inner end of the member. In the use of the device, the sac and member are first removed from the cup for receiving an eye wash solution. The member is then inserted into a sleeve so that the shoulder bears against the outer edge of the sleeve. As the sac is gripped and collapsed, the liquid solution in the sac is gradually forced through the reduced end of the tube and hence against the eye of the user.

U.S. Pat. No. 1,557,620 discloses an eye cup, a syringe bulb having a tubular extension extending through the bottom of the eye cup, a tubular member having one closed end and an open and adapted to be inserted in the tubular extension of the syringe bulb. The tubular member includes restricted orifices disposed within the eye cup.

SUMMARY OF THE INVENTION

The present invention relates to an eye drop dispensing device for use with a pliable ophthalmic solution container retaining an ophthalic solution therein including a dispensing nozzle.

More specifically, the eye drop dispensing device comprises a pliable housing having a channel formed therethrough to receive and house the dispensing nozzle and a major portion of the pliable ophthalmic solution container. An eyelid engaging rim including an outer arcuate or convex surface is formed on one end of the pliable housing to engage the user's face and eyelid as described more fully hereinafter.

To use, a pliable ophthalmic solution container is inserted or placed into the channel such that the dispensing nozzle is disposed immediately adjacent the eyelid engaging rim. So assembled, the outer arcuate or convex surface of the eyelid engaging rim is placed against the user's face and eyelid to hold the eyelid open and to properly align the dispensing nozzle with the user's eye.

Drops of the ophthalmic solution are then dispensed into the user's eye by depressing or squeezing the pliable housing which, in turn, squeezes the pliable ophthalmic solution container forcing drops of the ophthalmic solution therefrom. Since the dispensing nozzle is adjacent the eyelid engaging rim, the drops of ophthalmic solution fall gently onto the user's eye.

The invention accordingly comprises the features of construction, combination of elements, and arrangement of parts which will be exemplified in the construction hereinafter set forth, and the scope of the invention will be indicated in the claims.

BRIEF DESCRIPTION OF THE DRAWINGS

For a fuller understanding of the nature and object of the invention, reference should be had to the following detailed description taken in connection with the accompanying drawings in which.

Similar reference characters refer to similar parts throughout the several views of the drawings.

DETAILED DESCRIPTION OF THE PREFERRED EMBODIMENT

Figure 1:
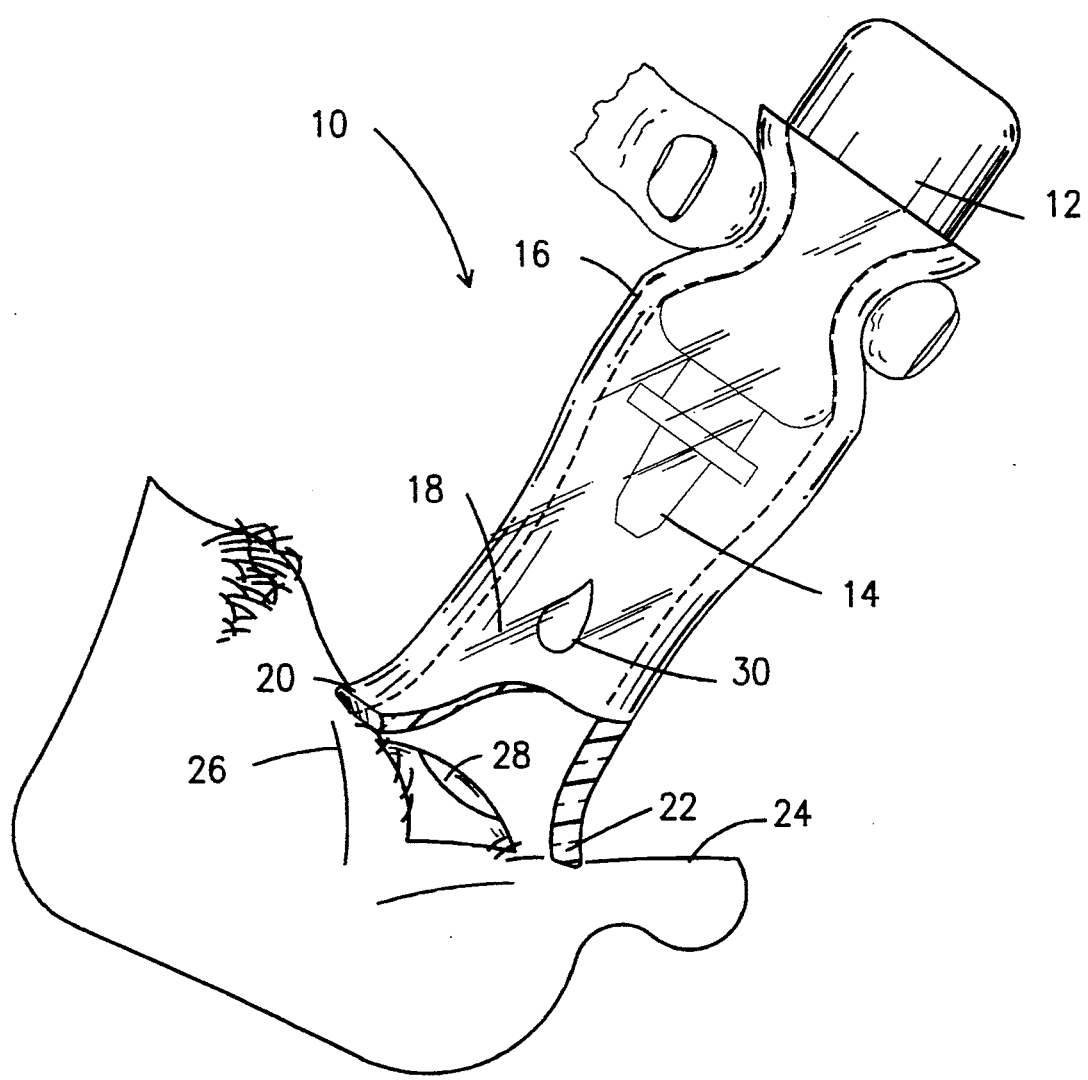
FIG. 1 is a cross-sectional side view of the eye drop dispensing device to dispense or administer eye drops.
Figure 2:
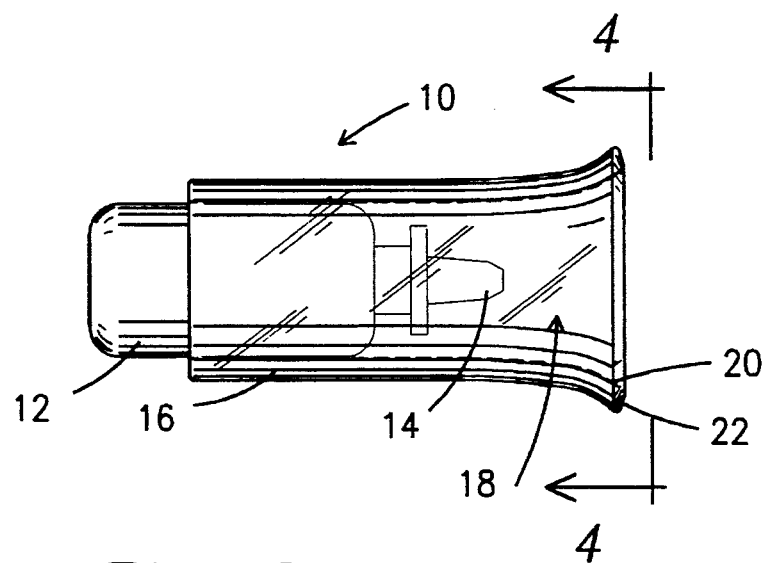
FIG. 2 is a cross-sectional top view of the eye drop dispensing device.
Figure 3:
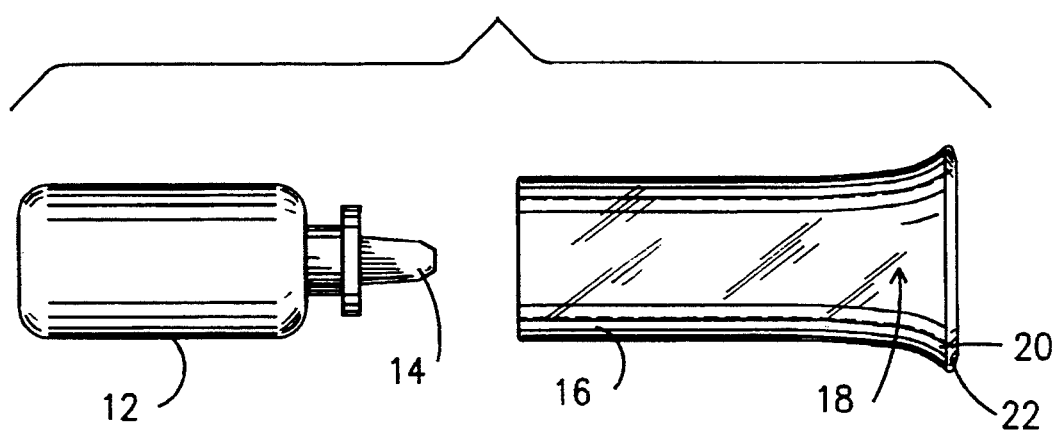
FIG. 3 is a cross-sectional side view of the eye drop dispensing device.
Figure 4:
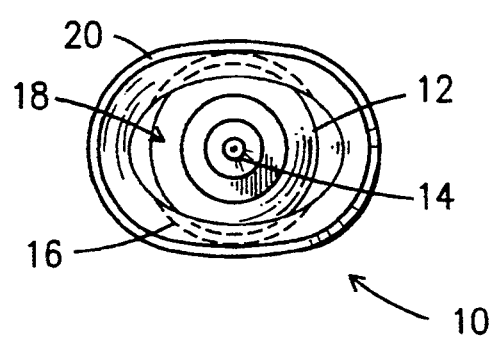
FIG. 4 is an end view of the eye drop dispensing device.

As shown in FIGS. 1 through 4, the present invention relates to an eye drop dispensing device generally indicated as 10 for use with a pliable ophthalmic solution container 12 that retains an ophthalmic solution therein and including a dispensing nozzle 14.

More specifically, the eye drop dispensing device 10 comprises a pliable substantially oval housing 16 having a substantially oval channel 18 formed therethrough to receive and house the dispensing nozzle 14 and a major portion of the pliable ophthalmic solution container 12. A substantially oval eyelid engaging rim 20 including an outer arcuate or convex surface 22 is formed on one end of the pliable substantially oval housing to engage the user's face 24 and eyelid 26 as described more fully hereinafter.

The eye drop dispensing device 10 is preferably constructed of flexible polymer, silicone or rubber with a hardness of between 30 and 80 durometers to permit the pliable substantially oval housing 16 to conform to the shape and size of the plastic ophthalmic solution container 12.

To use, the pliable ophthalmic solution container 12 is inserted or placed into the substantially oval channel 18 such that the dispensing nozzle 14 is disposed immediately adjacent the substantially oval eyelid engaging rim 20. So assembled, the outer arcuate or convex surface 22 of the substantially oval eyelid engaging rim 20 is placed against the user's face 24 and eyelid 26 to hold the eyelid 26 open and to properly aligning the dispensing nozzle 14 with the user's eye 28.

Drops 30 of the ophthalmic solution are then disposed into the user's eye 28 by depressing or squeezing the pliable substantially oval housing 16 which, in turn, squeezes the pliable ophthalmic solution container 12 forcing drops 30 of the ophthalmic solution therefrom. Since the dispensing nozzle 14 is adjacent the substantially oval eyelid engaging rim 20, the drops 30 of ophthalmic solution fall gently onto the user's eye 28.

It will thus be seen that the objects set forth above, among those made apparent from the preceding description are efficiently attained and since certain changes may be made in the above construction without departing from the scope of the invention, it is intended that all matter contained in the above description or shown in the accompanying drawing shall be interpreted as illustrative and not in a limiting sense.

It is also to be understood that the following claims are intended to cover all of the generic and specific features of the invention herein described, and all statements of the scope of the invention which, as a matter of language, might be said to fall therebetween.

Now that the invention has been described,
What is claimed is:

1. A method for dispensing eye drops into a user's eye through the use of an eye drop dispensing device including a pliable compressible hollow tubular housing movable between a first uncompressed and second compressed position having a distal end portion and a proximal end portion formed on opposite ends thereof including a channel having a distal opening and a proximal opening formed at opposite ends thereof to operatively house a dispensing nozzle and a major portion of a pliable ophthalmic solution container therein, and a skirt having a proximal end with a proximal skirt opening and a distal end with a distal skirt opening extending outwardly from said proximal end portion and including a skirt channel in open communication with said channel wherein the cross-sectional area of said skirt channel increases from said distal end to said proximal end such that the circumference of said proximal skirt-opening is greater than the circumference of said distal skirt opening, said method comprising inserting the pliable opthalmic solution container having an opthalmic solution therein into the channel, aligning a dispensing nozzle of the pliable ophthalmic solution container in spaced relationship relative to the person's eye by placing the proximal end of the shirt on the user's face in surrounding relationship relative the eye to be treated and dispensing eye drops directly into the user's eye through the nozzle by squeezing the pliable compressible hollow tubular housing so that the housing moves from said first position to said second position, thereby compressing the pliable opthalmic solution container.

* * * * *